(12) United States Patent
van Dort

(10) Patent No.: US 11,400,274 B2
(45) Date of Patent: Aug. 2, 2022

(54) HEART SUPPORT DEVICE WITH DIRECTIONAL FLOW ASSIST

(71) Applicant: Stichting Katholieke Universiteit, Nijmegen (NL)

(72) Inventor: Daniel Immanuel Michaël van Dort, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 12 days.

(21) Appl. No.: 17/263,554

(22) PCT Filed: Jul. 26, 2019

(86) PCT No.: PCT/NL2019/050499
§ 371 (c)(1),
(2) Date: Jan. 27, 2021

(87) PCT Pub. No.: WO2020/022905
PCT Pub. Date: Jan. 30, 2020

(65) Prior Publication Data
US 2021/0244935 A1    Aug. 12, 2021

(30) Foreign Application Priority Data

Jul. 27, 2018 (NL) .................................. 2021401

(51) Int. Cl.
*A61M 60/17* (2021.01)
*A61M 60/148* (2021.01)
(Continued)

(52) U.S. Cl.
CPC .......... *A61M 60/17* (2021.01); *A61M 60/148* (2021.01); *A61M 60/268* (2021.01);
(Continued)

(58) Field of Classification Search
CPC .. A61M 60/17; A61M 60/268; A61M 60/497; A61M 60/148; A61M 60/812; A61M 2206/16
(Continued)

(56) References Cited

U.S. PATENT DOCUMENTS 5,169,378 A * 12/1992 Figuera ............... A61M 60/268
600/16
5,820,542 A * 10/1998 Dobak, III ............ A61M 60/43
600/16

(Continued)

*Primary Examiner* — Erin M Piateski
(74) *Attorney, Agent, or Firm* — N.V. Nederlandsch Octrooibureau

(57) ABSTRACT

A heart support device for circulatory assistance is disclosed. The device comprises a chamber body (10) defining a chamber having an internal volume configured to be filled with blood. The chamber body (10) has a first opening (12) and the chamber is dimensioned such that the first opening (12) and the chamber are fully disposed within a chamber of the human heart. A dynamic volume body (14) is provided and configured to be inflated or deflated to alternately increase or decrease the interior volume of the chamber. A catheter (16) comprising at least one lumen in fluid communication with the dynamic volume body is configured to deliver fluid to the dynamic volume body to inflate the dynamic volume body. A directional flow structure is configured to direct a flow of blood out of the chamber in a direction substantially aligned with a direction in which the catheter (16) extends.

18 Claims, 10 Drawing Sheets

(51) Int. Cl.
  *A61M 60/268* (2021.01)
  *A61M 60/497* (2021.01)
  *A61M 60/812* (2021.01)

(52) U.S. Cl.
  CPC ........ *A61M 60/497* (2021.01); *A61M 60/812* (2021.01); *A61M 2206/16* (2013.01)

(58) Field of Classification Search
  USPC .......................................................... 606/18
  See application file for complete search history.

(56) References Cited

U.S. PATENT DOCUMENTS

| | | | | |
|---|---|---|---|---|
| 5,827,171 A | * | 10/1998 | Dobak, III | .......... A61M 60/135 |
| | | | | 600/16 |
| 2005/0228211 A1 | * | 10/2005 | Leasure | ................ A61M 60/40 |
| | | | | 600/16 |

* cited by examiner

HEART SUPPORT DEVICE WITH DIRECTIONAL FLOW ASSIST

FIELD OF THE INVENTION

The present invention relates to a heart support device, in particular to an intraventricular assistive pumping device with directional flow for circulatory assistance.

BACKGROUND

Following cardiac shock or due to chronic heart failure, it may be necessary to provide temporary mechanical circulatory assistance. Circulatory assistance can be provided by introducing a balloon into a heart chamber of a patient and causing the balloon to inflate and deflate during diastole and systole respectively. An external pumping unit is often used to inflate the balloon with a drive fluid (e.g. a neutral drive gas, or a liquid). Periodic inflation and deflation of the balloon within the heart chamber displaces the blood within the chamber and provides circulatory assistance to the patient.

Inflatable intraventricular devices are known in the art.

US patent publication US 2013/184515 A1, which describes an intraventricular balloon device comprising a slender flexible catheter with a proximal end and a distal end. An inflatable balloon is provided near the distal end and the balloon can be brought into its deflected state allowing entry into e.g. the left ventricle. An additional balloon can be provided on the catheter to be lodged within an appropriate blood vessel (e.g. the descending aorta).

International patent publication WO2016/001218 describes a heart support device for circulatory assistance with an internal member configured to be disposed within a heart lumen. The device comprises a dynamic volume body that can be inflated and deflated periodically with the natural (or modified) heart rhythm. The internal member has a substantially stiff wall strengthening portion arranged to engage an inner wall surface of the heart in operation and a dynamic member that is inflatable to assist pumping action of the heart.

Although the effect of both of the above described systems is to displace residual volume of blood from the heart lumen, such displacement devices do not approach the efficiency of natural cardiac motion.

There is thus a need for an improved circulatory assistance device.

SUMMARY OF THE INVENTION

The present invention seeks to provide an improved heart support device that can be implanted into a heart lumen with a minimally invasive procedure and is suitable for treating cardiogenic shock/and or chronic heart failure due to a weakened heart wall or scarring of the cardiac tissue and those for whom the risk of percutaneous cardiovascular intervention (PCI) is high. More particularly, the present invention seeks to improve upon existing devices by providing a directional flow structure to direct the flow of blood towards e.g. the aortic valve when the pump is placed in the left ventricle.

According to the present invention there is provided a heart support device for circulatory assistance comprising a chamber body defining a chamber having an internal volume configured to be filled with blood, the chamber body having a first opening, wherein the chamber body and the first opening are dimensioned to be disposed within a chamber of the human heart. A dynamic volume body is configured to be inflated and deflated to alternately increase and decrease the interior volume of the chamber. A catheter comprising at least one lumen is provided in fluid communication with the dynamic volume body and is arranged to deliver fluid to the dynamic volume body to inflate the dynamic volume body. A directional flow structure is also provided to direct a flow of blood out of the chamber in a direction substantially aligned with a direction in which the catheter extends. Since the device is configured for placement in the heart with the catheter extending through the aortic valve, by providing a directional flow device that directs the flow of expelled fluid along the axis of the catheter, the present invention provides directional flow towards the aortic valve in a manner that more closely mirrors natural flow of blood within the heart compared to known devices.

The directional flow structure can be configured in different ways. For example, the directional flow structure can comprise a restricted opening, e.g. a neck at the proximal end of the device that is relatively narrow compared to the chamber. The restricted opening can comprise an elongate tube, a tapered neck or a venturi tube (comprising a tapered inlet cone and a tapered outlet cone). The walls of the neck can be substantially parallel to each other.

Alternatively or additionally, the directional flow component can comprise a structure that imparts a vortex in the flow of fluid exiting the aperture. The vortex inducing structure can comprise static or movable impeller blades, a torsional balloon that expands with a twisting motion within the chamber, or a combination thereof.

The dynamic volume body can also be configured in different ways. For example, the dynamic volume body can comprise an inflatable membrane disposed within the chamber that is configured to expand within the chamber, thus displacing a volume of blood within the chamber through the aperture. In such embodiments the inflatable membrane can comprise a balloon having a membrane that is substantially more flexible relative to the walls of the chamber. This ensure that as the balloon inflates, it displaces the blood within the chamber, whilst the chamber maintains a stable expanded configuration.

The directional flow structure can comprise a restricted opening which provides a constriction at the first opening.

The heart support device can optionally comprising a support structure configured to support the chamber body in an expanded configuration.

In at least some embodiments, the heart support device may be collapsible to allow insertion of the device into a heart chamber in a minimally invasive manner. The support structure may be inflatable and can be provided in fluid communication with at least one lumen of the catheter to allow the support structure to be inflated.

In at least some embodiments, the support structure can comprise a scaffold formed of a resilient material, which is biased into a second configuration, and is expandable from a first configuration in which the chamber body has a first internal volume to the second configuration in which the chamber body comprises a second internal volume, the second internal volume being larger than the first internal volume.

Optionally, the dynamic volume body is configured to expand the support structure from the first configuration to the second configuration, thereby increasing the internal volume of the chamber.

In at least some embodiments, the dynamic volume body may comprise an inflatable balloon disposed within the chamber. Advantageously, the balloon may be a toroidal balloon.

The chamber body can extend from a proximal end at which the first aperture is located, to a distal end, opposite the proximal end, wherein the balloon is disposed at the distal end of the chamber body. The balloon may be configured to expand proximally to impart directional flow to the blood exiting the chamber.

The chamber body may be further provided with one or more additional openings, disposed at the distal end of the chamber, remote from the first openings. Additional openings at the distal end of the chamber may provide limited backflush from the distal end of the chamber, which can minimise the risk of blood pooling and clotting at the distal end of the chamber.

Advantageously, the additional opening(s) account for approximately 5%-10% (e.g. 5%) of the cross-sectional flow area into/out of the chamber, whilst the first opening(s) can account for approximately 90-95% (e.g. 95%).

Additionally or alternatively, the chamber walls can comprise one or more additional side openings configured to provide an additional inlet for blood into the interior of the chamber.

The additional openings can be configured as one-way flow opening(s) that allow flow into the interior volume of the chamber and prevent or inhibit flow out of the chamber.

In at least one group of invention embodiments, the device can further comprises a vortex inducing arrangement. The vortex inducing arrangement can be configured to impart a spiral or vortex flow to fluid exiting the chamber via the outlet opening.

The vortex inducing structure may comprises comprise a plurality of static blades arranged within the restricted opening.

In another group of embodiments, which may be implemented in isolation from or in combination with the embodiments described above, the chamber body can comprise a helical support structure configured to allow for helical collapse of the chamber body.

In yet another group of embodiments, which may be implemented in isolation from or in combination with the embodiments described above, the directional flow structure can comprises a venturi tube. This can maintain a steady directional flow of blood toward the aorta when the device is in use.

In yet another group of embodiments, which may be implemented in isolation from or in combination with the embodiments described above, the chamber body can comprise a longitudinal axis A, and the restricted opening can comprise a tube extending along a second axis, and wherein the first axis and the second axis are not coaxial. Such an arrangement can allow the chamber body to lie against the heart wall, whilst the outlet is position towards the aorta. This arrangement may further improve the directional flow of blood through the aortic valve. As described above, when the heart support device is positioned in the left ventricle, the directional flow structure is configured to direct the flow of blood toward the aortic valve. This may improve the efficiency of the device because it more closely replicates the blood flow seen during uncompromised natural heart function. Moreover, because the heart support device is positioned within the heart chamber, with the aperture located within the heart chamber, before the aortic valve, interference with (potentially resulting in damage to) the aortic valve is minimised.

BRIEF DESCRIPTION OF THE DRAWINGS

The present invention will now be described more fully with reference to a number of exemplary embodiments, as shown in the attached drawings in which.

DETAILED DESCRIPTION OF THE EXEMPLARY EMBODIMENTS

Figure 1:
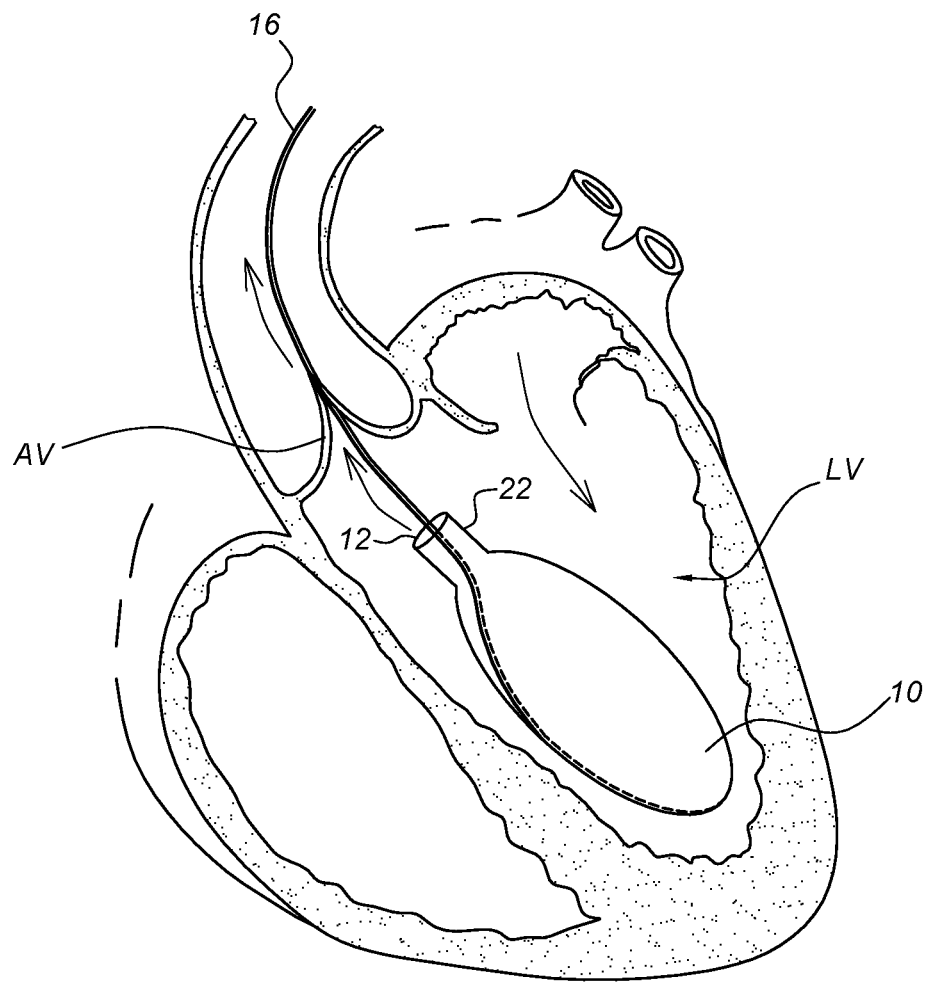
FIG. 1 shows a heart support device according to the present invention, in vivo.

FIG. 1 shows an exemplary embodiment of a heart support device for providing circulatory assistance to a patient. In the embodiment shown in FIG. 1, the heart support device is positioned within the left ventricle LV. As shown in FIG. 1, the heart support device according to the invention comprises a chamber 10 defining an internal volume and having at least one aperture 12 for fluid communication between the internal volume of the chamber 10 and a volume external to the chamber 10. As shown in FIG. 1, the chamber 10 is dimensioned so that the chamber 10 and the aperture 12 are disposed within a chamber of the human heart (in this case, the left ventricle LV).

In left ventricular embodiments, the device may have a maximum outer diameter of between 2 cm and 6 cm, more particularly 2 cm and 4 cm. In one example, the chamber has a maximum outer diameter at its widest point of 2.5 cm.

The length of the device (extending from the aperture to the end opposing the aperture) can be between 4 cm and 10 cm, more particularly between 5 cm and 8 cm. In one embodiment, the device has a length of 5 cm.

The skilled person will understand that the length of device can be adjusted to individual patient needs. For example, for many patients in need of circulatory assistance, the heart wall may be compromised to some degree, leading to a significant increase in the internal volume of the left ventricle compared to healthy individuals. Mapping can be carried out for individual patients can devices for according to individual needs. Alternatively, a range of sizes (small, medium, large) can be made and the appropriate size selected for each individual.

The support device further comprises at least one dynamic volume body 14, configured to be inflated and/or deflated to alternately increase and decrease the available interior volume of the chamber 10 (i.e. the volume within the chamber 10 that can be filled with blood). A catheter 16 comprising at least one fluid lumen 18 is in fluid communication with the dynamic volume body 14 and is configured to deliver fluid (e.g. a liquid, or a gas such as Helium) to the dynamic volume body 14 to inflate and/or deflate the body 14. A directional flow structure 20 is further provided to direct a flow of blood out of the chamber 10 in a direction substantially aligned with a direction in which the catheter extends.

In addition to displacing a volume of blood within the chamber 10 due to periodic increase/decrease the available volume of the chamber, the directional flow structure 20 advantageously directs the displaced blood in a direction of the aortic valve, i.e. in a manner that more closely approximates the natural function of the heart. By providing a directional flow structure to direct the flow of blood toward the aortic valve, the flow of blood created by the device more closely mimics the blood flow seen during uncompromised natural heart function, thereby improving the efficiency of the supported heart.

Directional flow structures can be realised in different ways. For example, the directional flow structure 20 can comprise a restricted opening at the proximal end of the chamber 10 (e.g. a neck). The proximal end of the chamber 10 is the end from which the catheter 16 extends. The restricted opening 22 has a smaller cross-sectional area than the cross-sectional area of the chamber 10 and provides a constriction at the first opening. Advantageously, the restricted opening 22 has a diameter that is less than (or equal to) the diameter of the aorta (generally 30% or less of the diameter of the main body; in some examples between 0.3 cm and 2 cm, more particularly between 0.3 cm and 1.5 cm, more particularly 0.5 cm). Advantageously, the restricted opening 22 is centred on the catheter 16 and comprises a straight sided tube or conduit. The tube can be cylindrical (with parallel walls) or tapered towards the opening. In some embodiments, a venturi tube forms the restricted opening, as described in more detail below.

Directional flow can also be provided by a structure that provides a pumping impulse in the direction of the aortic valve. Embodiments of the present invention comprising different directional flow structures will be described in more detail below.

The heart support device can further comprise a support structure 24 configured to support the chamber 10 in an expanded configuration. The support structure 24 can hold the chamber 10 in a stable position such that a balloon or other inflatable member can be inflated within the chamber 10 to decrease the available volume (thus forcing blood through the directional flow structure).

To allow the support device to be advanced into the heart lumen via a minimally invasive procedure, the support structure 24 can be collapsible. This can allow the device to be advanced into the left ventricle through the aorta (or another natural lumen). The support structure can be biased into an expanded position and maintained in the collapsed position during insertion by way of a guide tube or other tool. As an example, the support structure 24 can comprise a shape memory material, e.g. in the form of a collapsible scaffold formed of nitinol or another shape memory material.

Once removed from the guide tube, the support structure 24 can return to its expanded configuration.

Alternatively, the support structure 24 can comprise an expandable scaffold that can be expanded with a supply of fluid or gas to the scaffold. In other words, in at least some embodiments, the support structure 24 is inflatable. In such embodiments, the support structure 24 can be provided in fluid communication with at least one lumen of the catheter 16 to allow the support structure 24 to be inflated after it has been advanced into the heart lumen.

Once the chamber has been expanded to its expanded position, the dynamic volume body can act as a displacement body which is disposed within the chamber, and is expandable to fill an increasing proportion of the internal volume of chamber 10. Because the displacement body (e.g. the balloon 26) is disposed within the chamber, as the balloon inflates, it displaces blood within the chamber, thus forcing it through the aperture 12 towards the aortic valve.

The support structure 24 can comprise a scaffold formed of a resilient material, which is biased into and expandable from a first configuration in which the chamber body 10 has a first internal volume to a second configuration in which the chamber body 10 comprises a second internal volume, which is larger than the first internal volume. The resilient material can comprise an elastic or shape-memory material that is biased into an expanded configuration and can be compressed or collapsed whilst the device it advanced through a natural lumen into the heart chamber. In these embodiments, the dynamic volume body 14 can be configured to expand the support structure 24 from the first configuration to the second configuration, thereby increasing the internal volume of the chamber 10.

Referring again to FIG. 2A, the dynamic volume body 12 can comprise an inflatable balloon 26 disposed within the chamber 10. The balloon 26 is disposed within the chamber body 10, which can take the form of a cup 28. The cup 28 is relatively rigid compared to the balloon 26, once it has been expanded to its expanded configuration. The balloon 26 is formed at least partially of a membrane defining an interior volume that is configured to expand upon an increase of fluid (e.g. liquid or gas) within the balloon 28. The membrane can be formed of an elastic material configured to stretch as the interior volume is filled with air, or the membrane can be substantially non-elastic. The cup 28 can be formed of an expandable scaffold 30 with sidewall(s) 32, which defines the volume of the chamber 10. The sidewalls of the cup can be formed in the manner described in WO2016/001218 A1, which is hereby incorporated by reference in its entirety. However, in light of the present disclosure, the skilled person will appreciate that other cup constructions are possible.

Figure 2A:
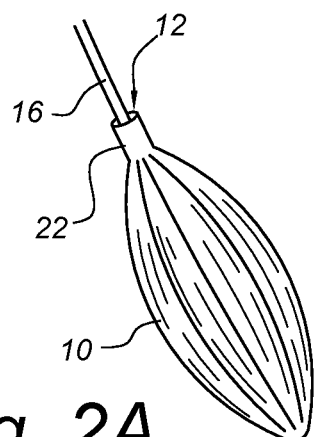
FIGS. 2A-2D show the operation of a heart support device according to embodiments of the invention.
Figure 2B:
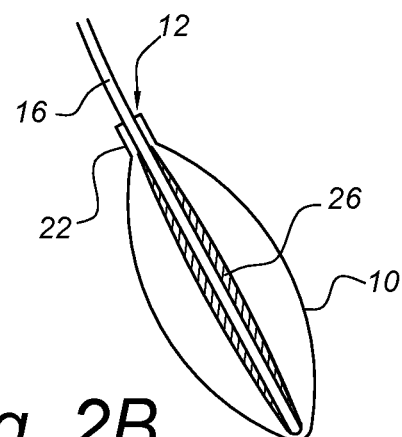
Figure 2C:
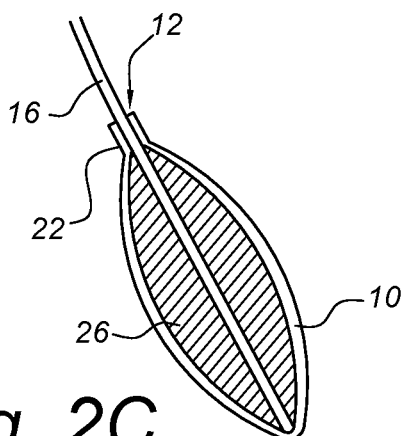
Figure 2D:
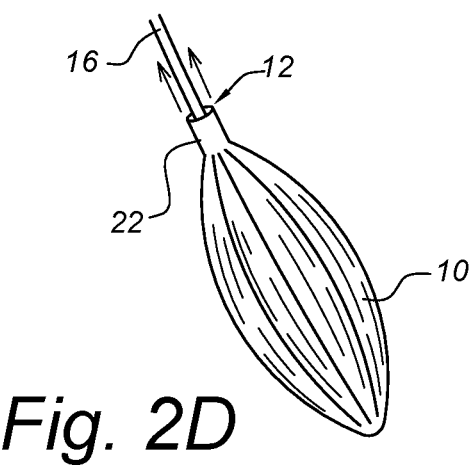

FIGS. 2B-2D illustrate the configuration of a 'balloon-in-cup' type of heart support device at different stages. In FIG. 2A, the cup 28 is in its expanded configuration within the heart lumen. The balloon 26 is empty and the interior volume of the chamber 10 is filled with blood B. In FIG. 5B, the balloon 26 is inflated by filling the balloon 26 with gas or liquid. As the balloon 26 inflates, the volume it occupies within the chamber 10 increases, and blood B is displaced from the interior volume of the chamber 10 and forced through the aperture 12 at the proximal end of the chamber. As shown in FIG. 2D, this causes blood to leave the chamber 10 via the aperture and the directional flow structure, thus direction the flow of blood towards the aortic valve AV. As the balloon 26 inflates, it occupies an increasing volume within the cup 28, thus displacing the blood filling the chamber 10 and forcing it from the chamber 10 through the directional flow structure and the aperture 12 towards the aortic valve AV.

Figure 3A:
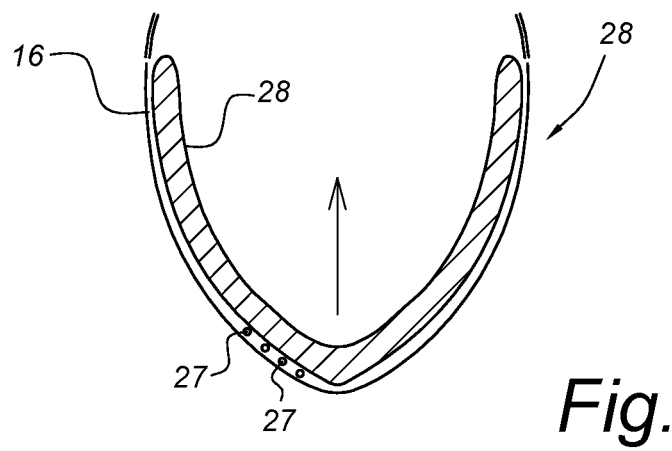
FIG. 3A shows a first balloon configuration suitable for use in embodiments of the present invention.

The balloon 26 can be configured in number of different ways. For example, the balloon 26 can comprise a balloon 26 that is free to expand in all directions (in the manner of a conventional balloon). As the balloon inflated within the chamber body 10, the available internal volume of the chamber decreases and blood is forced from the chamber 10 through the aperture 12. Alternatively, and as shown in FIG. 3A, the balloon 26 can comprise a flexible elastic membrane secured within the cup 28 to form a sealed cavity that can be filled with inflating fluid. The cup and membrane combination of embodiment can be formed in a similar manner to the device described in WO2016/001218 A1, except that the walls of the cup that forms the chamber body 10 should extend beyond the membrane towards the restricted opening that provides the directional flow control. Advantageously, the balloon 26 is provided at the opposite end of the chamber body 10 to the first opening 12.

Figure 3B:
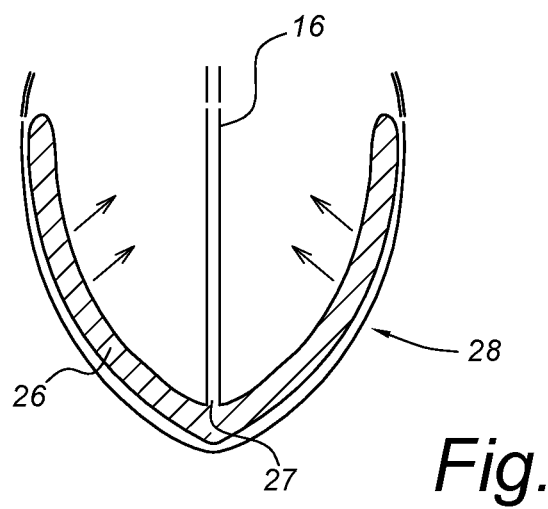
FIG. 3B shows a second balloon configuration suitable for use in embodiments of the present invention.
Figure 3C:
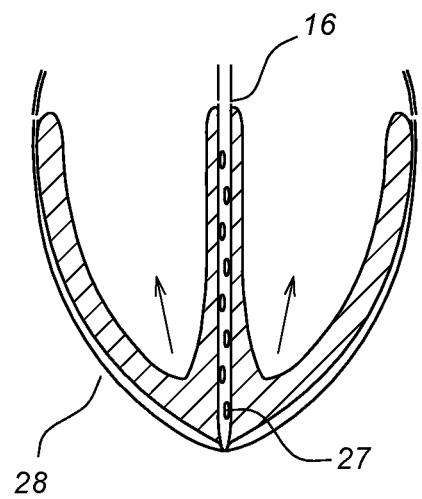
FIG. 3C shows a third balloon configuration suitable for use in embodiments of the present invention.

As shown in FIG. 3A, the cup 28 can incorporate a distal portion of the catheter 16 with a plurality of fluid ports 27 into its sidewall. The openings 27 are provided in fluid communication with the interior of the balloon 26 and are configured to fill the sealed cavity of the balloon 26. As shown in FIG. 3B, the balloon can be inflated and deflated by a catheter that is not incorporated into the sidewall. As shown in FIG. 3C, the balloon 26 can comprise a toroidal (or donut shaped) balloon 26. The toroidal balloon 26 can be configured to be centrally filled from a plurality of openings 27 in the catheter 16. This can provide symmetrical filling of the toroidal balloon 26.

As shown in FIGS. 3A and 3B, the chamber 10 can extend from a proximal end at which the first aperture 22 is located to a distal end, opposite the proximal end. The balloon 28 is disposed at the distal end of the chamber 10 and is configured to expand proximally. In both of the embodiments shown in FIGS. 3A and 3B, the balloon 28 is configured such that the flexible membrane expands (upon filling) in a direction towards the direction in which the catheter 16 extends. The extension of the flexible membrane in this direction can be configured to cause an impulse to further assist in directional flow control of blood leaving the chamber 10 through the aperture 12. In other words, the balloon 28 (or balloons) can be configured to inflate asymmetrically, expanding from the distal end toward the proximal end of the chamber 10.

Figure 4:
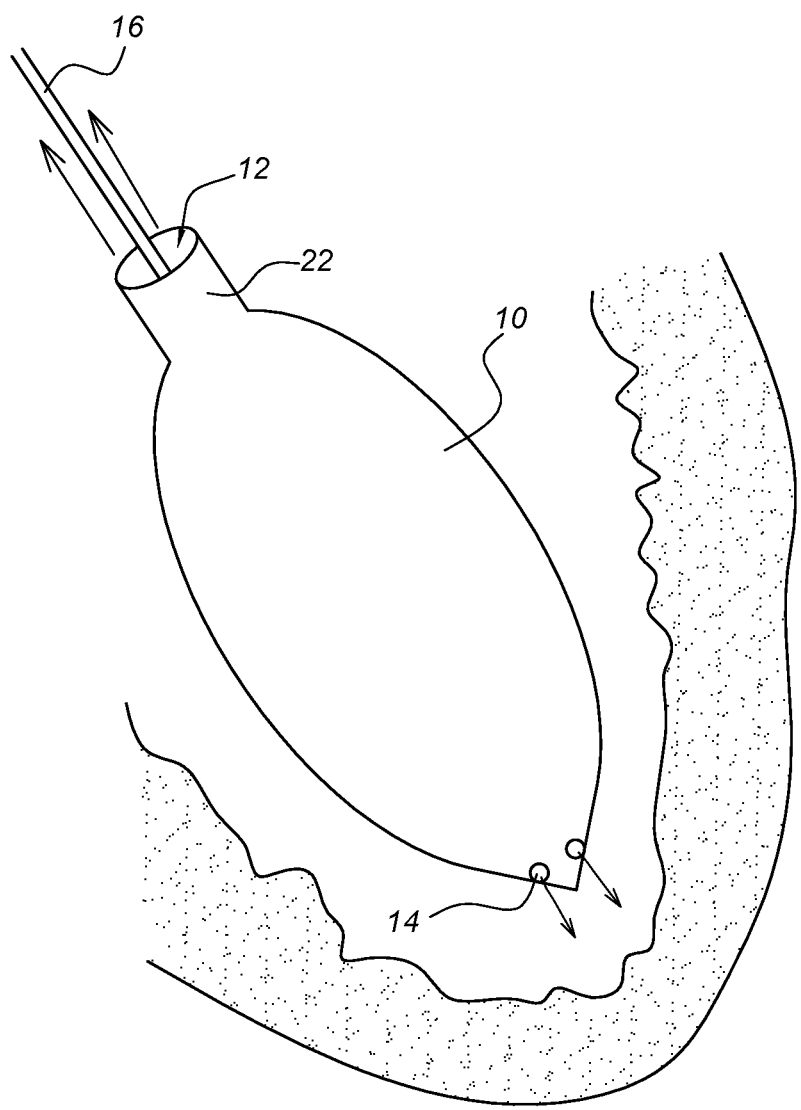
FIG. 4 shows a heart support device comprising a directional flow assembly according to an embodiment of the present invention.

Turning now to FIG. 4, the chamber 10 can be further provided with additional openings, disposed at the distal end of the chamber 10, remote from the first openings. The additional openings 30 provide additional fluid communication between the interior volume of the chamber 10 and the volume exterior to the chamber 10. Advantageously, the additional openings 30 allow blood from the lower part of the chamber 10 to be flushed through the additional openings 30 as the available volume of the chamber 10 decreases. By providing additional openings to flush blood from the lower part of the chamber 10, the risk of clots forming within the chamber 10 is decreased. Moreover, the flow of blood through the additional openings 30 flushes blood from the area A between the device and the heart wall, further reducing the risk of clots forming in the LV. Since the primary function of the heart support device is to provide circulatory assistance, the additional opening(s) 30 should be smaller than the first opening(s) 12, so that a majority of the blood expelled from the chamber 10 is expelled through the first opening(s) 12 towards the aorta. In some embodiments, the additional opening(s) 30 account for less than 30% of the cross-sectional flow area into/out of the chamber 10, whilst the first opening(s) 12 account for 70% or more. Advantageously, the additional opening(s) 30 account for approximately 5%-10% (e.g. 5%) of the cross-sectional flow area into/out of the chamber 10, whilst the first opening(s) 12 account for approximately 90-95% (e.g. 95%). The skilled person will appreciate that this ratio can be modified to suit the particular application/specific patient needs.

Figure 5:
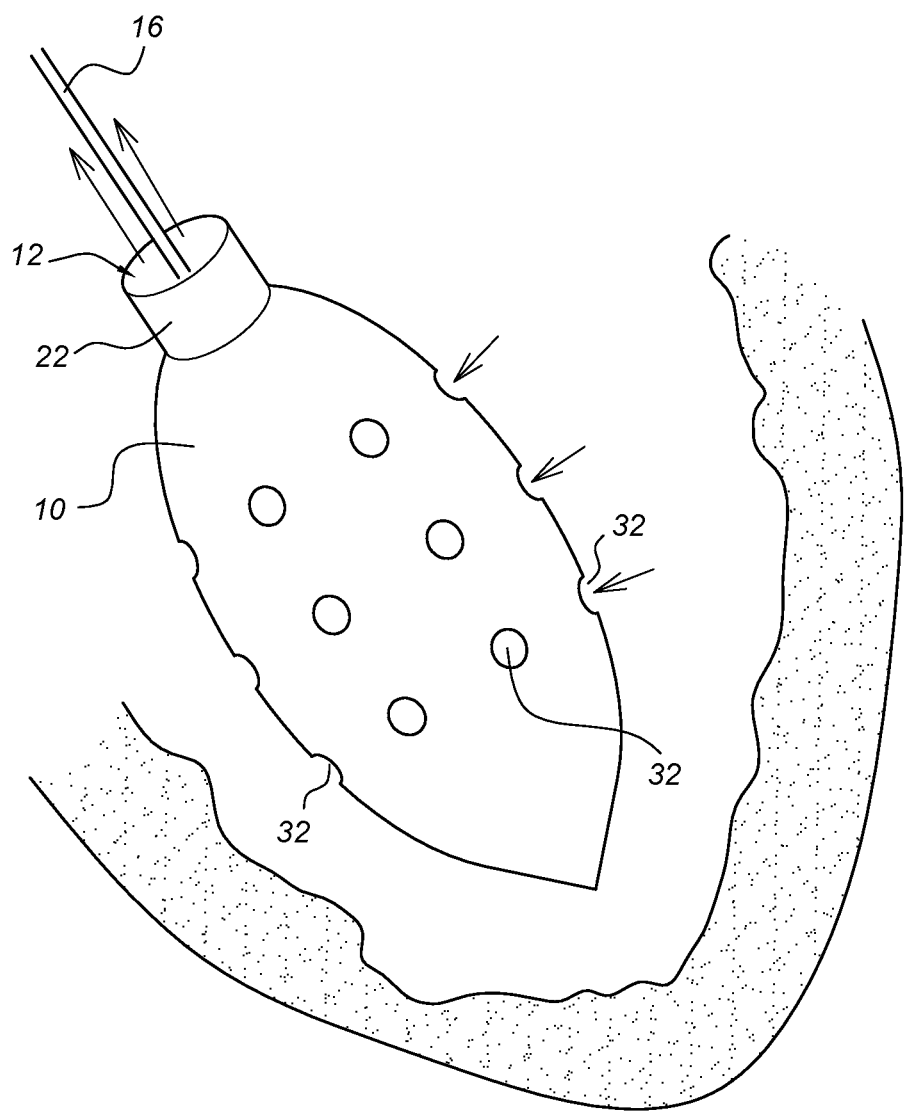
FIG. 5 shows a heart support device comprising a directional flow assembly according to an embodiment of the present invention.

Turning now to FIG. 5, the chamber 10 can comprise one or more additional side openings 32 configured to provide an additional inlet for blood into the interior of the chamber 10. The additional side openings 32 can comprise one-way valve structures configured to allow the flow of fluid into the chamber 10 via the openings 32 (and prevent flow in the opposite direction). By providing additional side openings 32 on the wall of the chamber 10, the heart support device can draw blood into the chamber 10 as the available volume increases from a location within the heart lumen that is remote from the aortic valve. This may prevent undesirable negative pressure behind the aortic valve.

Figure 6A:
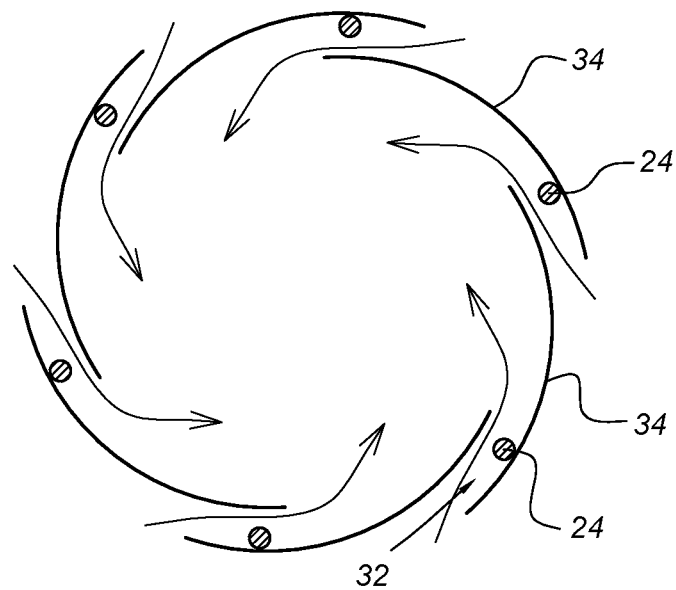
FIG. 6A-6D show the operation of a valve arrangement suitable for use in the embodiment shown in FIG. 5.
Figure 6B:
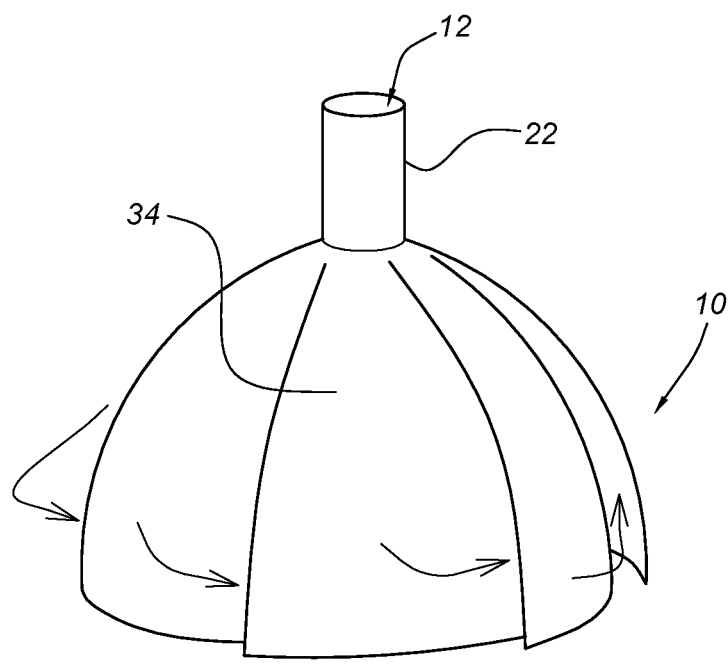
Figure 6C:
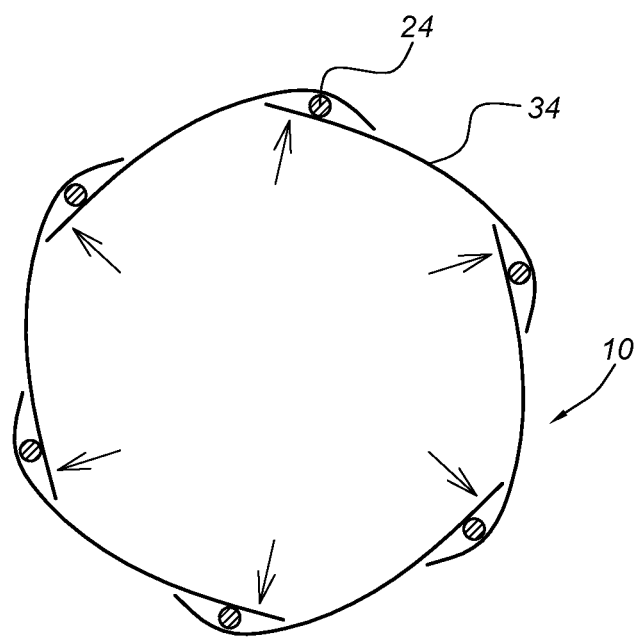
Figure 6D:
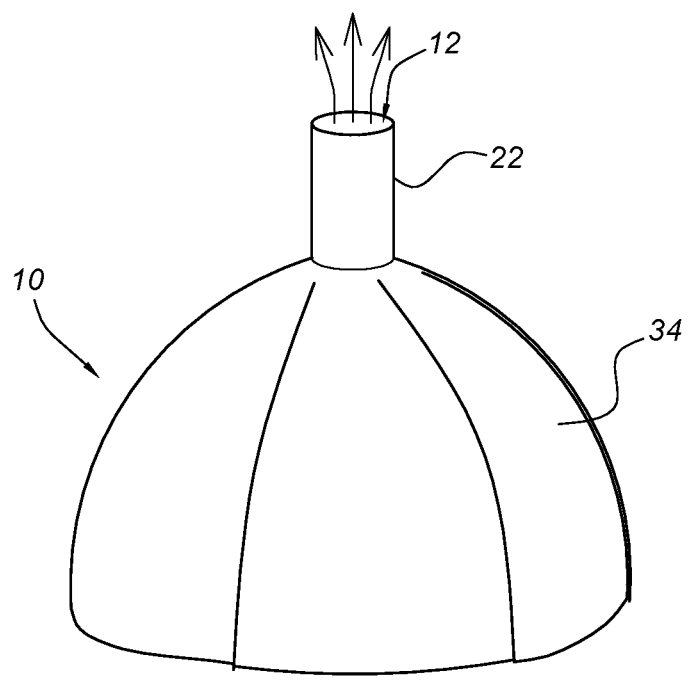

The additional side openings 32 can be configured to be self-sealing as the pressure within the chamber 10 increases with the decreasing available volume. As shown in FIG. 6A-6D, the additional side openings 32 can be formed at the intersection of a plurality of overlapping panels 34. The panels 34 are arranged in a circular overlapping arrangement, with the leading edge 34a of each panel 34 overlapping the trailing edge 34b of the next panel 34. As shown in FIGS. 6A and 6B, as the available interior volume of the chamber 10 increases, the pressure within the chamber 10 drops and blood is drawn in through the openings 32 between the panels 34. However, as the available interior volume of the chamber 10 decreases, the pressure within the chamber 10 forces the overlapping portions of the panels 34 into contact with each other, thus sealing the openings 32 shut (see FIG. 6C). The blood within the chamber 10 is thus forced out of the chamber 10 through the opening 12, as shown in FIG. 6D. As shown in FIGS. 6A to 6D, the panels 34 can be supported by a plurality of ribs that provide support structure 24.

As an alternative to the panel arrangement shown in FIGS. 6A-6D, the additional openings 32 (e.g. see FIG. 5) can comprise conventional one-way valves. The skilled person will appreciate that other constructions that allow one way flow through the openings 32 can also be employed. In other words, the additional openings can be configured as one-way flow opening(s) 32 that allow flow into the interior volume of the chamber 10 and prevent or inhibit flow out of the chamber 10.

Figure 7:
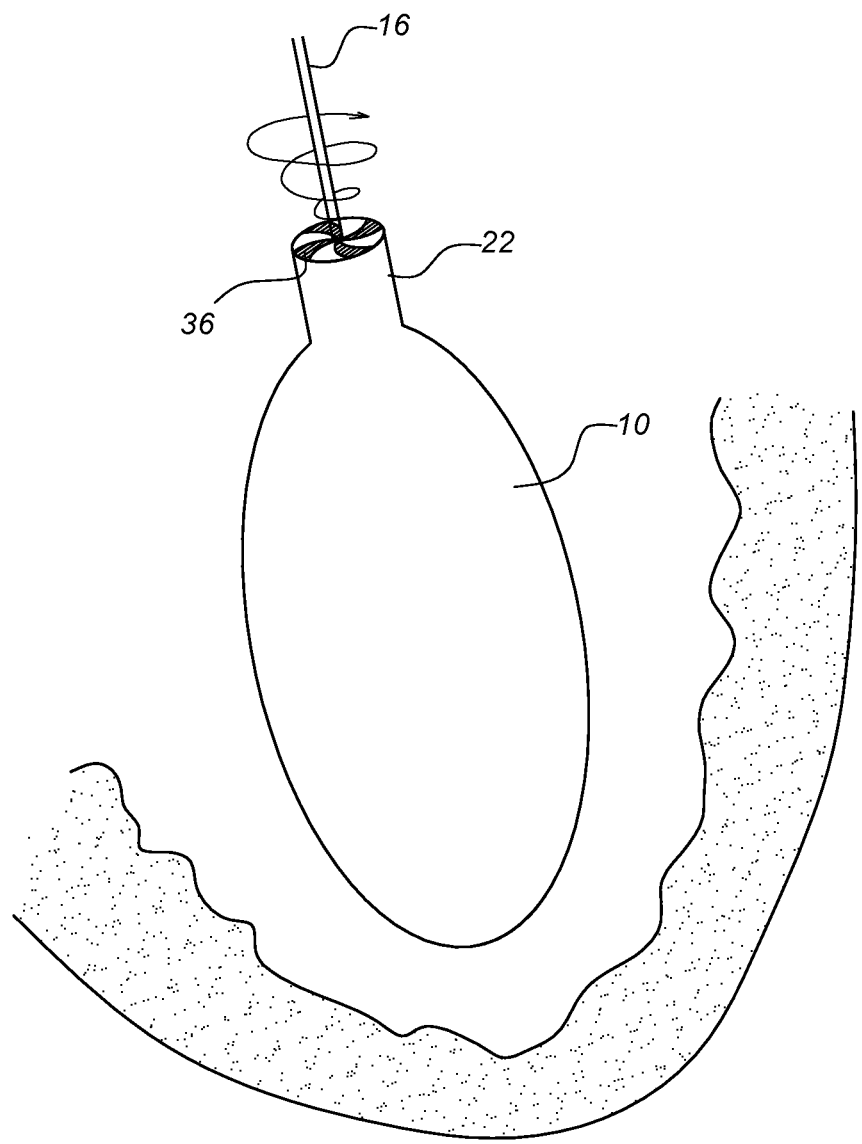
FIG. 7 shows a heart support device comprising a directional flow assembly according to another embodiment of the present invention.

To further enhance the directional flow out of the chamber 10 towards the aortic valve, the directional flow structure 20 can further comprise a vortex inducing arrangement. As shown in FIG. 7, the vortex inducing structure can comprise a plurality of static blades 36 arranged within the restricted opening 22 (e.g. a static impeller arrangement) configured to induce a vortex in the fluid that flows over the blades.

In other embodiments, a vortex or spiral flow towards the aorta can be induced by the manner in which the balloon 26 expands. For example, the balloon 26 can be wrapped or folded within the chamber such that upon expansion is twists to produce a vortex if flow through the aperture.

Figure 8:
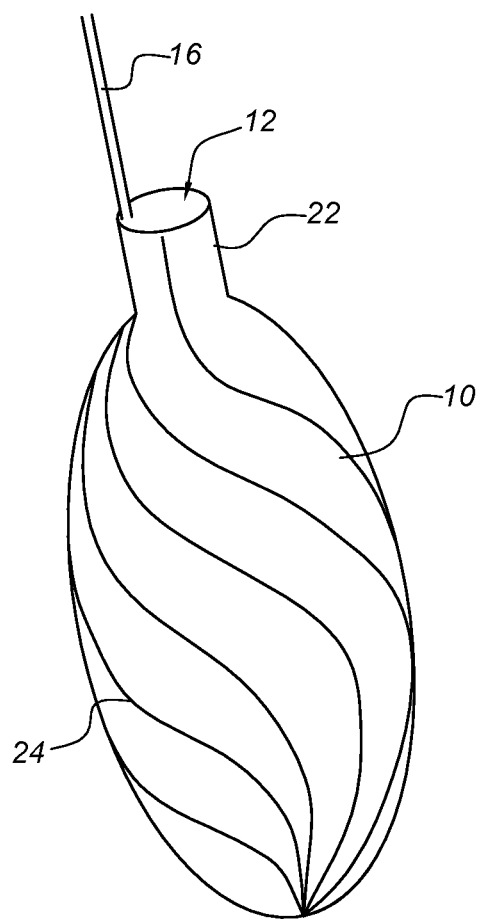
FIG. 8 shows a heart support device comprising a directional flow assembly according to another embodiment of the present invention.

In the embodiment shown in FIG. 8, the support device comprises a chamber 10 formed by a series of panels 34 supported by a support structure 24. The support structure 24 comprises a plurality of ribs 36 that are arranged in a helical fashion, extending from a first common end point 38 and, advantageously, meeting at a second common end point 40 (for example, as shown in FIG. 8). The support structure 24 is configured to be collapsed and expanded (during insertion of the device) by twisting the walls of the chamber 10 relative to the axis defined between the common end points 38, 40. The relative rotation of the walls of the chamber about the axis can be between 45 degree and 90 degrees, although other rotations are possible.

In any of the above described embodiments, the directional flow structure can be configured as a venturi tube. The venturi tube can comprise a restricted opening at the exit of the chamber body 10 that comprises an entry cone, a constriction, and an exit cone. In one example, the entry cone can comprise a cone of approximately 30 degrees, whilst the exit cone can comprise a cone of approximately 5 degrees.

Figure 9:
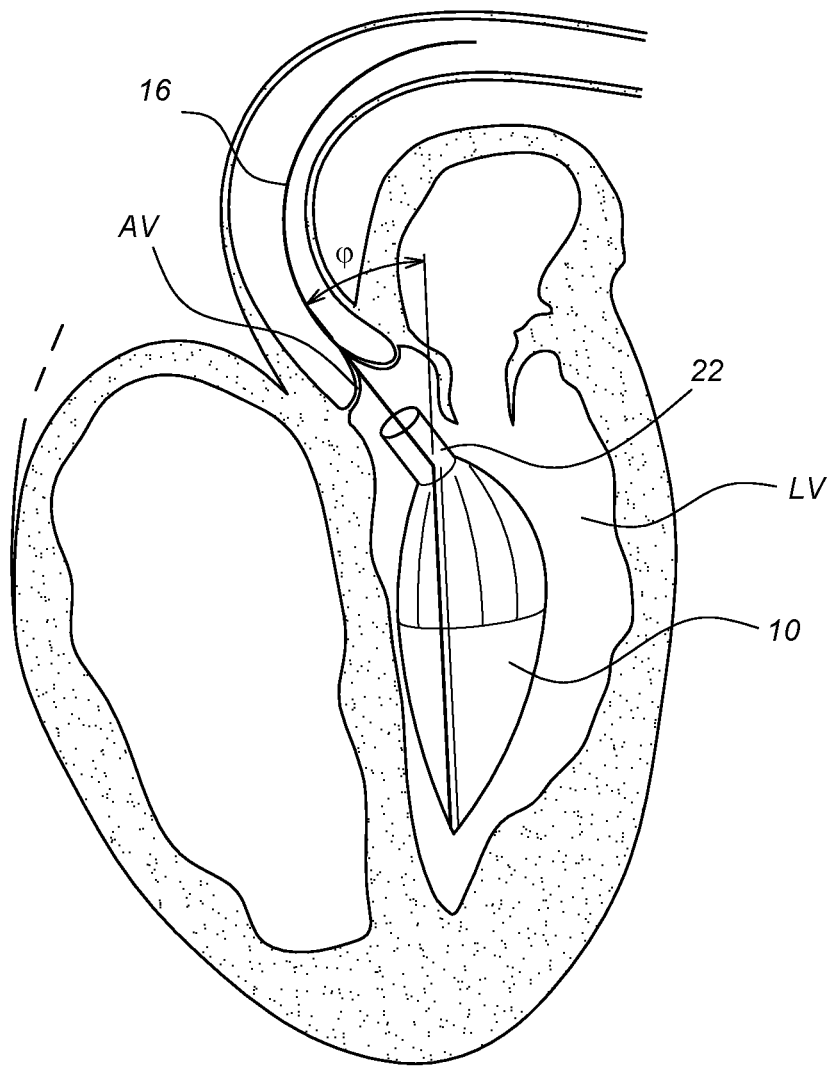
FIG. 9 shows an in vivo heart support device comprising an angled directional flow assembly.

As shown in FIG. 9, to further optimise the directional flow of blood out of the chamber 10, the restricted opening 22 can be angled with respect to the chamber body 10. For example, the chamber body 10 can comprise a longitudinal axis A, and the restricted opening 22 can comprise a tube that extends along a second axis B, which is not coaxial with the first axis A. The angle φ between the restricted opening 22 and the longitudinal axis of the chamber body 10 can be between 20 and 50 degrees, more particularly approximately 35 degrees. This angle allows the chamber body 10 to lie against the wall the left ventricle without obstructing the mitral valve MV, whilst still directing the flow of blood from the chamber 10 directly towards the aortic valve AV.

Methods of providing circulatory assistance comprising the above described device also form part of the present disclosure. For example, a method of providing circulatory assistance comprises the steps of placing the device 10 with a chamber of the heart such that the aperture of the device and associated directional flow components are disposed within the heart chamber, on a chamber side of the aortic valve. Once placed, the method comprises alternately inflating and deflating the dynamic volume body to displace blood within the chamber such that it is expelled through the aperture in a direction of the aortic valve.

The present invention has been described with reference to exemplary embodiments designed for use in the left ventricle. However, the skilled person will understand that the invention behind the present disclosure can be applied to other chambers of the heart. For example, a heart support device according to the present invention can be optimised for use within the right ventricle, and the directional flow structure can direct the flow of blood out of the chamber 10 towards the pulmonary valve. The skilled person will also appreciate that the features of the one embodiment described herein can be combined with the features of one or more additional embodiments. The skilled person will understand that other modifications can be made to the exemplary embodiments without departing from the scope of the invention.

The invention further comprises the following embodiments;

Embodiment 1

A heart support device for circulatory assistance, the heart support device comprising:
a chamber body (10) defining a chamber having an internal volume configured to be filled with blood, the chamber body (10) having a first opening (12), wherein the chamber body (10) and the first opening (12) are dimensioned to be disposed within a chamber of the human heart;
a dynamic volume body (14) configured to be inflated or deflated to alternately increase or decrease the interior volume of the chamber;
a catheter (16) comprising at least one lumen in fluid communication with the dynamic volume body (14), and configured to deliver fluid to the dynamic volume body to inflate the dynamic volume body; and
a directional flow structure configured to direct a flow of blood out of the chamber in a direction substantially aligned with a direction in which the catheter (16) extends.

Embodiment 2

The heart support device according to Embodiment 1, wherein the directional flow structure comprises a restricted opening (22) which provides a constriction at the first opening (12).

Embodiment 3

The heart support device according to Embodiment 1 or 2, further comprising a support structure (24) configured to support the chamber body (10) in an expanded configuration.

Embodiment 4

The heart support device according to Embodiment 3, wherein the support structure (24) is collapsible.

Embodiment 5

The heart support device according to Embodiment 3 or 4, wherein the support structure (24) is inflatable and is provided in fluid communication with at least one lumen of the catheter (16) to allow the support structure (24) to be inflated.

Embodiment 6

The heart support device according to any of Embodiments 1 to 5, wherein the support structure (24) comprises a scaffold formed of a resilient material, which is biased into a second configuration, and is expandable from a first configuration in which the chamber body (10) has a first internal volume to the second configuration in which the chamber body (10) comprises a second internal volume, the second internal volume being larger than the first internal volume.

Embodiment 7

The heart support device according to Embodiment 6, wherein the dynamic volume body (14) is configured to expand the support structure (24) from the first configuration to the second configuration, thereby increasing the internal volume of the chamber (10).

Embodiment 8

The heart support device according to any of Embodiments 1 to 5, wherein the dynamic volume body (14) comprises an inflatable balloon (28) disposed within the chamber (10).

Embodiment 9

The heart support device according to Embodiment 8, wherein the balloon (26) is a toroidal balloon (26).

Embodiment 10

The heart support device according to any of Embodiments 1 to 9, wherein the chamber body (10) extends from a proximal end at which the first aperture (12) is located, to a distal end, opposite the proximal end, wherein the balloon (26) is disposed at the distal end of the chamber body (10) and is configured to expand proximally.

Embodiment 11

The heart support device according to any of Embodiments 1 to 10, wherein the chamber body (10) is further provided with one or more additional openings (30), disposed at the distal end of the chamber 10, remote from the first openings.

Embodiment 12

The heart support device according to Embodiments 10, wherein the additional opening(s) (30) account for approximately 5%-10% (e.g. 5%) of the cross-sectional flow area into/out of the chamber, whilst the first opening(s) 12 account for approximately 90-95% (e.g. 95%).

Embodiment 13

The heart support device according to any of Embodiments 1 to 12, wherein the chamber body (10) can comprise one or more additional side openings (32) configured to provide an additional inlet for blood into the interior of the chamber (10).

Embodiment 14

The heart support device according to Embodiment 13, wherein the additional openings are configured as one-way flow opening(s) (32) that allow flow into the interior volume of the chamber (10) and prevent or inhibit flow out of the chamber (10).

Embodiment 15

The heart support device according to any of the preceding Embodiments, wherein the device further comprises a vortex inducing arrangement.

Embodiment 16

The heart support device according to Embodiment 15, wherein the vortex inducing structure comprises comprise a plurality of static blades (36) arranged within the restricted opening (22).

Embodiment 17

The heart support device according to any preceding Embodiment, wherein the chamber body (10) comprises a helical support structure (40) which is configured to allow for helical collapse of the chamber body (10).

Embodiment 18

The heart support device according to any preceding Embodiment, wherein the directional flow structure comprises a venturi tube.

Embodiment 19

The heart support device according to any of the preceding Embodiments, wherein the chamber body (10) comprises a longitudinal axis (A), and wherein the restricted opening (22) comprises a tube extending along a second axis (B), and wherein the first axis and the second axis are not coaxial.

The invention claimed is:

1. A heart support device for circulatory assistance, the heart support device comprising:
 a chamber body defining a chamber having an internal volume configured to be filled with blood, the chamber body having a first opening, wherein the chamber body and the first opening are dimensioned to be disposed within a chamber of the human heart;
 a dynamic volume body configured to be inflated or deflated to alternately increase or decrease the interior volume of the chamber;
 a catheter comprising at least one lumen in fluid communication with the dynamic volume body, and configured to deliver fluid to the dynamic volume body to inflate the dynamic volume body; and
 a directional flow structure configured to direct a flow of blood out of the chamber in a direction substantially aligned with a direction in which the catheter extends; and
 the device further comprises a vortex inducing arrangement.

2. The heart support device according to claim 1, wherein the directional flow structure comprises a restricted opening which provides a constriction at the first opening.

3. The heart support device according to claim 1, further comprising a support structure configured to support the chamber body in an expanded configuration.

4. The heart support device according to claim 3, wherein the support structure is collapsible.

5. The heart support device according to claim 3, wherein the support structure is inflatable and is provided in fluid communication with at least one lumen of the catheter to allow the support structure to be inflated.

6. The heart support device according to claim 1, further comprising a support structure, wherein the support structure comprises a scaffold formed of a resilient material, which is biased into a second configuration, and is expandable from a first configuration in which the chamber body has a first internal volume to the second configuration in which the chamber body comprises a second internal volume, the second internal volume being larger than the first internal volume.

7. The heart support device according to claim 6, wherein the dynamic volume body is configured to expand the support structure from the first configuration to the second configuration, thereby increasing the internal volume of the chamber.

8. The heart support device according to claim 1, wherein the dynamic volume body comprises an inflatable balloon disposed within the chamber.

9. The heart support device according to claim 8, wherein the balloon is a toroidal balloon.

10. The heart support device according to claim 8, wherein the chamber body extends from a proximal end at which the first opening is located, to a distal end, opposite the proximal end, wherein the balloon is disposed at the distal end of the chamber body and is configured to expand proximally.

11. The heart support device according to claim 1, wherein the chamber body is further provided with one or more additional openings, disposed at the distal end of the chamber, remote from the first openings.

12. The heart support device according to claim 11, wherein the one or more additional openings account for approximately 5%-10% of the cross-sectional flow area into/out of the chamber, whilst the first opening(s) account for approximately 90-95%.

13. The heart support device according to claim 1, wherein the chamber body can comprise one or more additional side openings configured to provide an additional inlet for blood into the interior of the chamber.

14. The heart support device according to claim 13, wherein the additional openings are configured as one-way flow opening(s) that allow flow into the interior volume of the chamber and prevent or inhibit flow out of the chamber.

15. The heart support device according to claim 1, wherein the vortex inducing structure comprises comprise a plurality of static blades arranged within the restricted opening.

16. The heart support device according to claim 1, wherein the chamber body comprises a helical support structure which is configured to allow for helical collapse of the chamber body.

17. The heart support device according to claim 1, wherein the directional flow structure comprises a venturi tube.

18. The heart support device according to claim 1, wherein the chamber body comprises a longitudinal axis (A), and wherein the restricted opening comprises a tube extending along a second axis (B), and wherein the first axis and the second axis are not coaxial.

* * * * *

UNITED STATES PATENT AND TRADEMARK OFFICE
CERTIFICATE OF CORRECTION

PATENT NO. : 11,400,274 B2
APPLICATION NO. : 17/263554
DATED : August 2, 2022
INVENTOR(S) : Daniël Immanuel Michaël van Dort It is certified that error appears in the above-identified patent and that said Letters Patent is hereby corrected as shown below:

On the Title Page

Item (72), in Column 1, in "Inventor", Line 1, delete "Daniel" and insert -- Daniël --, therefor.

In the Claims

In Column 13, in Claim 15, Line 15, delete "comprises comprise" and insert -- comprises --, therefor.

Signed and Sealed this
Twenty-fifth Day of October, 2022

Katherine Kelly Vidal
*Director of the United States Patent and Trademark Office*